United States Patent
Hoegger

(10) Patent No.: US 10,537,104 B2
(45) Date of Patent: Jan. 21, 2020

(54) INSECTICIDE MIXTURES COMPRISING LOLINE ALKALOIDS

(71) Applicant: SYNGENTA PARTICIPATIONS AG, Basel (CH)

(72) Inventor: Patrik Hoegger, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 16/099,131

(22) PCT Filed: May 2, 2017

(86) PCT No.: PCT/EP2017/060344
§ 371 (c)(1),
(2) Date: Nov. 5, 2018

(87) PCT Pub. No.: WO2017/191095
PCT Pub. Date: Nov. 9, 2017

(65) Prior Publication Data
US 2019/0313646 A1    Oct. 17, 2019

(30) Foreign Application Priority Data

May 6, 2016   (EP) ..................................... 16168648

(51) Int. Cl.
*A01N 43/90* (2006.01)
*A01N 43/40* (2006.01)

(52) U.S. Cl.
CPC ............. *A01N 43/90* (2013.01); *A01N 43/40* (2013.01)

(58) Field of Classification Search
CPC ................................. A01N 43/90; A01N 43/40
See application file for complete search history.

(56) References Cited

U.S. PATENT DOCUMENTS 5,185,028 A    2/1993 Powell et al.

FOREIGN PATENT DOCUMENTS

| WO | 2006068669 A1 | 6/2006 |
| WO | 2008111861 A1 | 9/2008 |
| WO | 2011117272 A2 | 9/2011 |

OTHER PUBLICATIONS

Wilkinson, Heather H. et al.; "Contribution of Fungal Loline Alkaloids to Protection from Aphids in a Grass-Endophyte Mutualism"; MPMI, vol. 13, No. 10; Oct. 1, 2000; pp. 1027-1033.
Reidell, W.E. et al.; "Naturally-occuring and synthetic loline alkaloid derivatives: Insect feeding behaviour modification and toxicity"; Journal of Asia Pacific Entemology, Korean Society of Applied Entemology, Suwon, KR; vol. 26, No. 1; Jan. 1, 1991; pp. 122-129.
Schardl, Christopher L. et al.; "Loline alkaloids: Currencies of mutualism"; Phytochemistry, Pergamon Press, GB; vol. 68, No. 7, Mar. 17, 2007; pp. 980-996.
International Search Report for PCT/EP2017/060344, dated Jun. 13, 2017.

*Primary Examiner* — Trevor Love

(74) *Attorney, Agent, or Firm* — Baker & Hostetler, LLP; Toni-Junell Herbert

(57) ABSTRACT

The present invention relates to pesticidal mixtures. In particular it relates to mixtures of loline alkaloids with other pesticides. Such mixtures are useful for the control of insect pests and for improving the yield of crop plants.

8 Claims, No Drawings

INSECTICIDE MIXTURES COMPRISING LOLINE ALKALOIDS

CROSS-REFERENCE TO RELATED APPLICATIONS

This application is a 371 National Stage application of International Application No. PCT/EP2017/060344, filed May 2, 2017, which claims priority to European Patent Application No. 16168648.0 filed May 6, 2016, the entire contents of which applications are hereby incorporated by reference.

The present invention relates to pesticidal mixtures. In particular it relates to mixtures of loline alkaloids with other pesticides. Such mixtures are useful for the control of insect pests and for improving the yield of crop plants.

Loline alkaloids are compounds that are produced through the symbiosis of fungal endophytes such as Epichloe or Neotyphodium with host plants such as meadow fescue, and have the chemical formula (I):

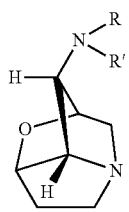

(I)

wherein:
R=H or $CH_3$ and
R'=H, $CH_3$, CHO, $COCH_3$.

In particular, loline alkaloids include loline (R=H, R'=$CH_3$), N-acetylloline (R=$CH_3$, R'=$COCH_3$), N-formylloline (R=CH3, R'=CHO), and N-acetylnorloline (R=H, R'=$COCH_3$). Some loline alkaloids have insecticidal activity.

According to the present invention, there is provided a composition comprising (A) at least one loline alkaloid of formula (I), and (B) a pesticide.

Component (A) may be any loline alkaloid of formula (I), or a mixture of more than one loline alkaloid of formula (I). In particular, the at least one loline alkaloid is selected from the group consisting of N-acetylloline (NAL), N-formylloline (NFL), and N-acetylnorloline (NANL). In certain embodiments, component (A) may include more than one loline alkaloid selected from the group consisting of N-acetylloline (NAL), N-formylloline (NFL), and N-acetylnorloline (NANL) in any combination. Optionally, component (A) may include further loline alklaoids.

In certain embodiments, component (A) is NAL, NFL and NANL (A1), NAL and NFL (A2), NAL and NANL (A3), NFL and NANL (A4), NAL (A5), NFL (A6), or NANL (A7). Preferably component (A) comprises N-acetylloline and N-formylloline.

In one embodiment, component (A) comprises N-acetylloline, N-formylloline and N-acetylnorloline.

In one aspect of the present invention, when component (A) comprises N-acetylloline, N-formylloline and N-acetylnorloline (A1), the weight ratio of the three loline analogs is from 1:3:1 to 1:6:3.

In particular, the present invention includes the following weight ratios of N-acetylloline, N-formylloline and N-acetylnorloline, namely 1:3:1, 1:3:2, 1:3:3, 1:4:1, 1:4:2, 1:4:3, 1:5:1, 1:5:2, 1:5:3, 1:6:1, 1:6:2, 1:6:3 and all ratios in between.

In one embodiment, the weight ratio of N-acetylloline, N-formylloline and N-acetylnorloline in (A) is about 1:4:2.

Methods for producing loline alkaloids are known in the art. WO2008/111861 describes methods for extracting loline alkaloids from endophyte-infected plant material. Blankenship et al. ((2001) Phytochemistry 58, 395-401) describes the production of loline alkaloids by fermentation of fungal endophytes in chemically defined growth media.

Component (B) may be any known active ingredient, for example as disclosed in the Pesticide Manual (The Pesticide Manual—A World Compendium; Seventeenth edition; Editor: C. D. S. Tomlin; The British Crop Protection Council). In particular, component (B) may be an acaricide, bactericide, fungicide, herbicide, insecticide, miticide, molluscicide, nematicide, plant activator, plant growth regulator, biostimulant, rodenticide, safener, synergist, crop enhancing agent or an active ingredient that improves tolerance of plants to abiotic stress conditions. Component (B) may be a chemical or a biological pesticide.

In one embodiment, component (B) is an insecticide such as abamectin, acequinocyl, acetamiprid, acrinathrin, afidopyropen, afoxalaner, alanycarb, allethrin, alpha-cypermethrin, alphamethrin, amidoflumet, azadirachtin, azocyclotin, Bacillus firmus, Bacillus thuringiensis, Beauveria bassiana, bensultap, benzoximate, betacyfluthrin, bifenazate, binapacryl, bioallethrin, bioallethrin S-cyclopentyl isomer, bioresmethrin, bifenthrin, broflanilide, brofluthrinate, bromophos-ethyl, buprofezine, cadusafos, carbaryl, carbosulfan, cartap, chlorantraniliprole, chlorfenapyr, chloropralethrin, chromafenozide, cloethocarb, clothianidin, cyantraniliprole, cyclaniliprole, cycloprothrin, cycloxaprid, Cydia pomonella granulosis virus, cyenopyrafen, cyflumetofen, cyfluthrin, cyhalodiamide, cyhalothrin, cypermethrin, cyphenothrin, cyromazine, deltamethrin, demeton-S-methyl, diafenthiuron, dialifos, dibrom, dicloromezotiaz, diflovidazine, diflubenzuron, dinactin, dinocap, dinotefuran, d-limonene, emamectin, empenthrin, epsilon-metofluthrin, epsilon-momfluorothrin, esfenvalerate, ethion, ethiprole, etofenprox, etoxazole, famphur, fenazaquin, fenfluthrin, fenobucarb, fenoxycarb, fenpropathrin, fenpyroximate, fenvalerate, fipronil, flometoquin, flonicamid, floupyram, fluacrypyrim, fluazaindolizine, fluazuron, flubendiamide, flucythrinate, flupyradifurone, fluensulfone, flufenerim, flufenprox, flufiprole, fluhexafon, flumethrin, flupyradifurone, fluralaner, fluvalinate, fluxametamide, fosthiazate, gamma-cyhalothrin, gossyplure, guadipyr, halofenozide, halofenprox, harpin, Helicoverpa armigera nucleopolyhedrovirus, Helicoverpa zea nucleopolyhedrovirus, Heliothis virescens nucleopolyhedrovirus, Heliothis punctigera nucleopolyhedrovirus, hexythiazox, hydramethylnon, imicyafos, imidacloprid, imiprothrin, indoxacarb, iodomethane, isothioate, ivermectin, kappa-bifenthrin, kappa-tefluthrin, lambda-cyhalothrin, lepimectin, lufenuron, metaflumizone, metaldehyde, methomyl, methoxyfenozide, metofluthrin, milbemectin, niclosamide, nitenpyram, oxamyl, parathion-ethyl, Pasteuria nishizawae, p-cymene, permethrin, phenothrin, phosphocarb, piperonylbutoxide, pirimicarb, pirimiphos-ethyl, Plutella xylostella granulosis virus, Plutella xylostella nucleopolyhedrovirus, polyhedrosis virus, prallethrin, profenofos, propargite, propetamphos, protrifenbute, pyflubumide, pymetrozine, pyraclofos, pyrafluprole, pyrethrum, pyridaben, pyridalyl, pyrifluquinazon, pyrimidifen, pyriprole, pyriproxyfen, QRD-420 terpenoid blend, QR-452 terpenoid blend, QRD-460 terpenoid blend, selamectin, silafluofen, spinetoram, spinosad, spirodiclofen, spiromesifen, spirotetramat, *Spodoptera frugiperda* nucleopolyhedrovirus, sulfoxaflor, tebufenozide, tebufenpyrad, tefluthrin, terpenoid blends, terpenoids, tetradiphon, tetramethrin, tetranactin, tetraniliprole, theta-cypermethrin, thiacloprid, thiamethoxam, thiodicarb, tioxazafen, tolfenpyrad, transfluthrin, trichlorfon, triflumezopyrim, zeta-cypermethrin, α-terpinene, 4-[(5S)-5-(3,5-dichloro-4-fluoro-phenyl)-5-(trifluoromethyl)-4H-isoxazol-3-yl]-N-[(4R)-2-ethyl-3-oxo-isoxazolidin-4-yl]-2-methyl-benzamide, or [3-(4-chloro-2,6-dimethyl-phenyl)-8-methoxy-1-methyl-2-oxo-1,8-diazaspiro[4.5]dec-3-en-4-yl] ethyl carbonate.

Preferably when component (B) is an insecticide, it is selected from the list consisting of abamectin, acetamiprid, azadirachtin, *Bacillus thuringiensis*, buprofezine, cartap, chlorantraniliprole, chlorfenapyr, clothianidin, cyantraniliprole, diafenthiuron, emamectin benzoate, ethiprole, flonicamid, flupyradifurone, imidacloprid, indoxacarb, lambda cyhalothrin, lufenuron, methoxyfenozide, *Helicoverpa armigera* nucleopolyhedrovirus, profenofos, pymetrozine, pyrethrum, QRD-460 terpenoid blend, spinosad, spirodiclofen, spiromesifen, spirotetramat, sulfoxaflor, tefluthrin, thiacloprid, thiamethoxam, thiodicarb, fluxametamide, 4-[(5S)-5-(3,5-dichloro-4-fluoro-phenyl)-5-(trifluoromethyl)-4H-isoxazol-3-yl]-N-[(4R)-2-ethyl-3-oxo-isoxazolidin-4-yl]-2-methyl-benzamide, [3-(4-chloro-2,6-dimethylphenyl)-8-methoxy-1-methyl-2-oxo-1,8-diazaspiro[4.5]dec-3-en-4-yl] ethyl carbonate and *Beauveria bassiana*.

More preferably, when component (B) is an insecticide it is selected from the group consisting of abamectin, *Bacillus thuringiensis*, chlorantraniliprole, cyantraniliprole, flonicamid, flupyradifurone, pyrethrum, QRD-460 terpenoid blend, spinosad, spirodiclofen, spiromesifen, spirotetramat, sulfoxaflor, 4-[(5S)-5-(3,5-dichloro-4-fluoro-phenyl)-5-(trifluoromethyl)-4H-isoxazol-3-yl]-N-[(4R)-2-ethyl-3-oxo-isoxazolidin-4-yl]-2-methyl-benzamide, or [3-(4-chloro-2,6-dimethyl-phenyl)-8-methoxy-1-methyl-2-oxo-1,8-diazaspiro[4.5]dec-3-en-4-yl] ethyl carbonate and thiamethoxam.

More preferably, when component (B) is an insecticide it is selected from the group consisting of abamectin (B1), chlorantraniliprole (B2), cyantraniliprole (B3), flonicamid (B4), spinosad (B5), spiromesifen (B6), spirotetramat (B7), and thiamethoxam (B8).

In one embodiment, component (B) is selected from the group consisting of flonicamid and thiamethoxam.

In one embodiment, component (B) is abamectin.

In one embodiment, component (B) is chlorantraniliprole.

In one embodiment, component (B) is cyantraniliprole.

In one embodiment, component (B) is flonicamid.

In one embodiment, component (B) is spinosad.

In one embodiment, component (B) is spiromesifen.

In one embodiment, component (B) is spirotetramat.

In one embodiment, component (B) is thiamethoxam.

In a different embodiment, component (B) is a fungicide such as acibenzolar-S-methyl, aflaguard, aldimorph, ametoctradin, amisulbrom, anilazine, azaconazole, azoxystrobin, *Bacillus subtilis* strain QST 713, benalaxyl, benalaxyl-M, benodanil, benomyl, benthiavalicarb, benzothiostrobin, benzovindiflupyr, binapacryl, biphenyl, bitertanol, bixafen, blad, blasticidin-, boscalid, bromuconazole, captafol, captan, carbendazim, carboxin, carpropamid, chloroneb, chlorothalonil, chlozolinate, copper different salts, coumoxystrobin, cyazofamid, cyflufenamid, cymoxanil, cyproconazole, cyprodinil, dichlobentiazox, dichlofluanid, diclocymet, diclomezine, dicloran, diethofencarb, difenoconazole, diflumetorim, dimethirimol, dimethomorph, dimoxystrobin, diniconazole, dinocap, dipymetitrone, dithianon, dodemorph, dodine, edifenphos, enoxastrobin, epoxiconazole, plant essential oil, ethaboxam, ethirimol, etridiazole, famoxadone, fenamidone, fenaminstrobin, fenarimol, fenbuconazole, fenfuram, fenhexamid, fenoxanil, fenpropidin, fenpropimorph, fenpyrazamine, fentin acetate, fentin chloride, fentin hydroxide, ferbam, ferimzone, fluazinam, fludioxonil, flufenoxystrobin, fluindapyr, flumetralin, flumorph, fluopicolide, fluopyram, fluoxastrobin, fluquinconazole, flusilazole, flusulfamide, flutianil, flutolanil, flutriafol, fluxapyroxad, folpet, fosetyl-Al, fthalide, fuberidazole, furametpyr, guazatine, hexaconazole, hymexazole, imazalil, imibenconazole, iminoctadine, inatreq, iodocarb, ipconazole, ipfentrifluconazole, iprobenfos, iprodione, iprovalicarb, isofetamid, isoprothiolane, isopyrazam, isotianil, jiaxiangjhunzi, kasugamycin, kresoximmethyl, laminarin, mancozeb, mandestrobin, mandipropamid, maneb, mefentrifluconazole, mepanipyrim, mepronil, meptyldinocap, metalaxyl, metalaxyl-M, metconazole, methasulfocarb, methyl, metiram, metominostrobin, metrafenone, myclobutanil, naftifine, nuarimol, octhilinone, ofurace, orysastrobin, oxathiapiprolin, oxolinic acid, oxpoconazole, oxycarboxin, oxytetracycline, paclobutrazol, pefurazoate, penconazole, pencycuron, penflufen, penthiopyrad, phenamacril, phophorous acid and salts, picarbutrazox, picoxystrobin, piperalin, polyoxin, probenazole, prochloraz, procymidone, propamocarb, propiconazole, propineb, proquinazid, prothiocarb, prothioconazole, pydiflumetofen, pyraclostrobin, pyrametostrobin, pyraoxystrobin, pyraziflumid, pyrazophos, pyribencarb, pyributicarb, pyrifenox, pyrimethanil, pyrimorph, pyriofenone, pyrisoxazole, pyroquilon, quinofumelin, quinoxyfen, quintozene, sedaxane, Serenade, silthiofam, simeconazole, spiroxamine, streptomycin, Taegro, tebuconazole, tebufloquin, teclofthalam, tecnazene, terbinafine, tetraconazole, thiabendazole, thifluzamide, thiophanate, thiophanate-methyl, thiram, tiadinil, tolclofos-methyl, tolprocarb, tolylfluanid, triadimefon, triadimenol, triazoxide, triclopyricarb, tricyclazole, tridemorph, trifloxystrobin, triflumizole, triforine, trinexapac-ethyl, triticonazole, validamycin, valifenalate, vinclozolin, zineb, ziram, zoxamide.

Preferably when component (B) is a fungicide, it is selected from the list consisting of: acibenzolar-S-methyl, azoxystrobin, benzovindiflupyr, bixafen, boscalid, captan, chlorothalonil, cyproconazole, cyprodonil, difenoconazole, fenpropidin, fenpropimorph, fluazinam, fludioxonil, fluopyram, fluoxastrobin, fluxapyroxad, isopyrazam, mandipropamid, mefenoxam, metalaxyl, oxathiapoprolin, penconazole, penflufen, penthiopyrad, propiconazole, prothioconazole, pydiflumetofen, pyraclostrobin, sedaxane, tebuconazole, thiabendazole, thiram and trifloxystrobin.

More preferably, when component (B) is a fungicide it is selected from the list consisting of acibenzolar-S-methyl, azoxystrobin, benzovindiflupyr, difenoconazole, fludioxonil, metalaxyl-m, metalyxyl, oxathiapiprolin, pydiflumetofen, sedaxane and thiabendazole.

In a further embodiment, component (B) is a plant growth regulator such as 1-methylcyclopropene, 1-naphthol, 2,3,5-tri-iodobenzoic acid, 2,3-dihydro-5,6-diphenyl-1,4-oxath(II)ne, 2,4,5-T, 2,4-D, 2,4-DB, 2,4-DEP, 24-epi-brassinolide, 28-homobrassinolide, 2-cyano-3-(2,4-dichlorophenyl) acrylic acid, 2-hydrazinoethanol, 2iP, 4-CPA, 4-hydroxyphenethyl alcohol, abscisic acid, AC 94377, ACC, ancymidol, auxins, aviglycine, bachmedesh, benzofluor, benzyladenine, 24-epi-brassinolide, 28-homo-brassinolide, brassinolide, brassinolide-ethyl, brassinosteroids, BTS 44584, buminafos, butralin, calcium cyanamide, carbaryl, carvone, chlorfluren, chlorflurenol, chlormequat-chloride, chlorphonium, chlorpropham, choline chloride, ciobutide, clofencet, clofibric acid, cloprop, cloxyfonac, cyanamide, cyclanilide, cycloheximide, cyprosulfamide, cytokinins, daminozide, DCPTA, deoxystrigol, dicamba-methyl, dichlorflurenol, dichlorflurenol-methyl, dichlorprop, dikegulac, dimexano, endothal, epocholeone, etacelasil, ethephon, ethychlozate, ethylene, fenoprop, fenridazon, flumetralin, fluoridamid, flurenol, flurprimidol, forchlorfenuron, fosamine, fuphenthiourea, furalane, gibberellic acid, gibberellins, glyoxime, glyphosine, GR-24, heptopargil, hexafluoroacetone trihydrate, holosulf, hymexazol, IAA, IBA, Inabenfide, INCYDE, isoprothiolane, isopyrimol, jasmonates, jasmonic acid, karetazan, karrikins, kinetin, lead arsenate, maleic hydrazide, MCPB, mefluidide, mepiquat, merphos, methasulfocarb, metoxuron, N-(2-ethyl-2H-pyrazol-3-yl)-N'-phenylurea, N-m-tolylphthalamic acid, N-pyrrolidinosuccinamic acid, naphthaleneacetamide, naphthoxyacetic acids, n-decanol, nonanoic acid, N-phenylphthalamic acid, orobanchol, paclobutrazol, pentachlorophenol, piproctanyl, potassium naphthenate, polyamines, prohexadione-calcium, prohydrojasmon, propham, propyl 3-tert-butylphenoxyacetate, prosuler, pydanon, pyripropanol, salicylic acid, sintofen, sodium (Z)-3-chloroacrylate, sodium naphthenate, sorgolactone, strigol, strigolactones, tecnazene, tetcyclacis, thidiazuron, tiaojiean, triacontanol, triapenthenol, tribufos, trinexapac, trinexapac-ethyl, uniconazole, zeatin, α-naphthaleneacetic acid.

Preferably when component (B) is a plant growth regulator, it is selected from the list consisting of 1-methylcyclopropene, brassinolide, brassinosteroid, chlormequat-chloride, ethephon, flurprimidol, jasmonate, mepiquat, paclobutrazol, prohexadione-calcium, strigolactone and trinexapac-ethyl. More preferably, when component (B) is a plant growth regulator it is selected from the list consisting of brassinolide, chlormequat chloride, flurprimidol, mepiquat, paclobutrazol, prohexadione-calcium and trinexapac-ethyl.

In a further embodiment, Component (B) is a product that enhances plant tolerance to abiotic stress. In particular there may be mentioned biostimulant products that contain one or more micronutrients, macronutrients, plant hormones, or amino acids. Examples of biostimulant products include seaweed extracts, Quantis™, Isabion™, Vitazyme™ Megafol™, Releaseed™, Biozyme™, TerraSorb™, Aminocore™, Radical™, Proplex™, Bio-Forge™, Terrabiogen™, Folicist™, Cytozyme™, Cytoplant™, and Greenstim™.

Preferably when component (B) is a product that enhances plant tolerance to abiotic stress, it is selected from the group consisting of Quantis™ and Isabion™.

In a further embodiment, Component (B) is a herbicide such as acetochlor, acifluorfen-sodium, aclonifen, alachlor, alloxydim, ametryn, amicarbazone, amidosulfuron, aminocyclopyrachlor, aminopyralid, amitrole, asulam, atrazine, bensulfuron-methyl, bentazone, bicyclopyrone, bifenox, bispyribac-sodium, bromacil, bromoxynil, butafenacil, cafenstrole, carfentrazone-ethyl, chlorimuron-ethyl, chlorotoluron, cinosulfuron, clethodim, clodinafop-propargyl, clomazone, clopyralid, cyhalofop-butyl, 2,4-D (including the choline salt and 2-ethylhexyl ester thereof), daimuron, desmedipham, dicamba (including the aluminum, aminopropyl, bis-aminopropylmethyl, choline, diglycolamine, dimethylamine, dimethylammonium, potassium and sodium salts thereof), diclofop-methyl, difenzoquat, diflufenican, diflufenzopyr, dimethachlor, dimethenamid-P, diquat dibromide, diuron, esprocarb, ethofumesate, fenoxaprop-P-ethyl, fenquinotrione, flazasulfuron, florasulam, fluazifop-P-butyl, flucarbazone-sodium, flufenacet, flumetralin, flumetsulam, flumioxazin, flupyrsulfuron-methyl-sodium, fluroxypyrmeptyl, fluthiacet-methyl, fomesafen, foramsulfuron, glufosinate (including the ammonium salt thereof), glyphosate (including the diammonium, isopropylammonium and potassium salts thereof), halauxifen-methyl, halosulfuron-methyl, haloxyfop-methyl, hexazinone, imazamox, imazapic, imazapyr, imazaquin, imazethapyr, indaziflam, iodosulfuron-methyl-sodium, iofensulfuron, iofensulfuron-sodium, ioxynil, ipfencarbazone, isoxaben, isoxaflutole, lactofen, linuron, mecoprop-P, mefenacet, mesosulfuron, mesosulfuron-methyl, mesotrione, metamitron, metobromuron, metolachlor, metoxuron, metribuzin, metsulfuron, molinate, napropamide, nicosulfuron, norflurazon, orthosulfamuron, oxadiargyl, oxadiazon, oxyfluorfen, paraquat dichloride, pendimethalin, penoxsulam, phenmedipham, picloram, picolinafen, pinoxaden, pretilachlor, primisulfuron-methyl, prodiamine, prometryn, propachlor, propanil, propaquizafop, propham, propyzamide, prosulfocarb, prosulfuron, pyrasulfotole, pyrazolynate, pyrazosulfuron-ethyl, pyribenzoxim, pyridate, pyriftalid, pyrithiobac-sodium, pyroxasulfone, pyroxsulam, quinclorac, quizalofop-P-ethyl, rimsulfuron, saflufenacil, sethoxydim, S-metolachlor, sulcotrione, sulfentrazone, tebuthiuron, tefuryltrione, tembotrione, terbuthylazine, terbutryn, thiencarbazone, thifensulfuron, tiafenacil, tolpyralate, topramezone, tralkoxydim, triafamone, triasulfuron, tribenuron-methyl, triclopyr, trifloxysulfuron-sodium, trifludimoxazin, tritosulfuron.

In a further embodiment, Component (B) is a safener such as cloquintocet-mexyl, cyprosulfamide, dichlormid, fenchlorazole-ethyl, fenclorim, fluxofenim, isoxadifen-ethyl, mefenpyr-diethyl, N-(2-methoxybenzoyl)-4-[(methylaminocarbonyl)amino]benzenesulfonamide, oxabetrinil.

In another embodiment, Component (B) is an acaricide such as amitraz, chinomethionat, chlorobenzilate, cyenopyrafen, cyhexatin, dicofol, dienochlor, etoxazole, fenazaquin, fenbutatin oxide, fenpropathrin, fenpyroximate, hexythiazox, propargite, pyridaben, tebufenpyrad.

The composition may comprise more than one compound from component (B), thus forming a mixture comprising three or more active ingredients For example component (B) may be two insecticides, an insecticide and a fungicide, an insecticide and a plant growth regulator, a fungicide and a plant growth regulator, two fungicides, two plant growth regulators, and so on.

The composition may also include, or be applied in conjunction with, one or more beneficial organisms.

According to the present invention, there is provided a composition comprising (A) at least one loline alkaloid, and (B) a pesticide selected from the group consisting of flonicamid and thiamethoxam.

In one embodiment, component (A) comprises at least N-acetylloline (NAL) and N-formylloline (NFL).

In one embodiment, component (A) comprises N-acetylloline (NAL), N-formylloline (NFL), and N-acetylnorloline (NANL).

In one embodiment, component (A) comprises N-acetylloline (NAL), N-formylloline (NFL), and N-acetylnorloline (NANL) in a weight ratio from 1:3:1 to 1:6:3.

In one embodiment, component (A) comprises N-acetylloline (NAL), N-formylloline (NFL), and N-acetylnorloline (NANL) in a weight ratio of about 1:4:2.

In one embodiment, component (A) comprises N-acetylloline (NAL), N-formylloline (NFL), and N-acetylnorloline (NANL) in a weight ratio of 1:4:2.

In one embodiment of the present invention, the composition comprises NAL+NFL+NANL (A1) and an insecticide selected from the group consisting of abamectin (B1), chlorantraniliprole (B2), cyantraniliprole (B3), flonicamid (B4), spinosad (B5), spiromesifen (B6), spirotetramat (B7) and thiamethoxam (B8). In a further embodiment, the composition comprises NAL+NFL+NANL (A1) and an insecticide selected from the group consisting of flonicamid and thiamethoxam.

In one embodiment of the present invention, the composition comprises NAL+NFL (A2) and an insecticide selected from the group consisting of abamectin (B1), chlorantraniliprole (B2), cyantraniliprole (B3), flonicamid (B4), spinosad (B5), spiromesifen (B6), spirotetramat (B7) and thiamethoxam (B8). In a further embodiment, the composition comprises NAL+NFL (A2) and an insecticide selected from the group consisting of flonicamid and thiamethoxam.

In one embodiment of the present invention, the composition comprises NAL+NANL (A3) and an insecticide selected from the group consisting of abamectin (B1), chlorantraniliprole (B2), cyantraniliprole (B3), flonicamid (B4), spinosad (B5), spiromesifen (B6), spirotetramat (B7) and thiamethoxam (B8). In a further embodiment, the composition comprises NAL+NANL (A3) and an insecticide selected from the group consisting of flonicamid and thiamethoxam.

In one embodiment of the present invention, the composition comprises NFL+NANL (A4) and an insecticide selected from the group consisting of abamectin (B1), chlorantraniliprole (B2), cyantraniliprole (B3), flonicamid (B4), spinosad (B5), spiromesifen (B6), spirotetramat (B7) and thiamethoxam (B8). In a further embodiment, the composition comprises NFL+NANL (A4) and an insecticide selected from the group consisting of flonicamid and thiamethoxam.

In one embodiment of the present invention, the composition comprises NAL (A5) and an insecticide selected from the group consisting of abamectin (B1), chlorantraniliprole (B2), cyantraniliprole (B3), flonicamid (B4), spinosad (B5), spiromesifen (B6), spirotetramat (B7) and thiamethoxam (B8). In a further embodiment, the composition comprises NAL (A5) and an insecticide selected from the group consisting of flonicamid and thiamethoxam.

In one embodiment of the present invention, the composition comprises NFL (A6) and an insecticide selected from the group consisting of abamectin (B1), chlorantraniliprole (B2), cyantraniliprole (B3), flonicamid (B4), spinosad (B5), spiromesifen (B6), spirotetramat (B7) and thiamethoxam (B8). In a further embodiment, the composition comprises NFL (A6) and an insecticide selected from the group consisting of flonicamid and thiamethoxam.

In one embodiment of the present invention, the composition comprises NANL (A7) and an insecticide selected from the group consisting of abamectin (B1), chlorantraniliprole (B2), cyantraniliprole (B3), flonicamid (B4), spinosad (B5), spiromesifen (B6), spirotetramat (B7) and thiamethoxam (B8). In a further embodiment, the composition comprises NANL (A7) and an insecticide selected from the group consisting of flonicamid and thiamethoxam.

In particular, the following mixtures may be mentioned:
NAL+NFL+NANL (A1) with abamectin (B1), NAL+NFL+NANL (A1) with chlorantraniliprole (B2), NAL+NFL+NANL (A1) with cyantraniliprole (B3), NAL+NFL+NANL (A1) with flonicamid (B4), NAL+NFL+NANL (A1) with spinosad (B5), NAL+NFL+NANL (A1) with spiromesifen (B6), NAL+NFL+NANL (A1) with spirotetramat (B7), and NAL+NFL+NANL (A1) with thiamethoxam (B8);

NAL+NFL (A2) with abamectin (B1), NAL+NFL (A2) with chlorantraniliprole (B2), NAL+NFL (A2) with cyantraniliprole (B3), NAL+NFL (A2) with flonicamid (B4), NAL+NFL (A2) with spinosad (B5), NAL+NFL (A2) with spiromesifen (B6), NAL+NFL (A2) with spirotetramat (B7), and NAL+NFL (A2) with thiamethoxam (B8);

NAL+NANL (A3) with abamectin (B1), NAL+NANL (A3) with chlorantraniliprole (B2), NAL+NANL (A3) with cyantraniliprole (B3), NAL+NANL (A3) with flonicamid (B4), NAL+NANL (A3) with spinosad (B5), NAL+NANL (A3) with spiromesifen (B6), NAL+NANL (A3) with spirotetramat (B7), and NAL+NANL (A3) with thiamethoxam (B8);

NFL+NANL (A4) with abamectin (B1), NFL+NANL (A4) with chlorantraniliprole (B2), NFL+NANL (A4) with cyantraniliprole (B3), NFL+NANL (A4) with flonicamid (B4), NFL+NANL (A4) with spinosad (B5), NFL+NANL (A4) with spiromesifen (B6), NFL+NANL (A4) with spirotetramat (B7), and NFL+NANL (A4) with thiamethoxam (B8);

NAL (A5) with abamectin (B1), NAL (A5) with chlorantraniliprole (B2), NAL (A5) with cyantraniliprole (B3), NAL (A5) with flonicamid (B4), NAL (A5) with spinosad (B5), NAL (A5) with spiromesifen (B6), NAL (A5) with spirotetramat (B7), and NAL (A5) with thiamethoxam (B8);

NFL (A6) with abamectin (B1), NFL (A6) with chlorantraniliprole (B2), NFL (A6) with cyantraniliprole (B3), NFL (A6) with flonicamid (B4), NFL (A6) with spinosad (B5), NFL (A6) with spiromesifen (B6), NFL (A6) with spirotetramat (B7), and NFL (A6) with thiamethoxam (B8);

NANL (A7) with abamectin (B1), NANL (A7) with chlorantraniliprole (B2), NANL (A7) with cyantraniliprole (B3), NANL (A7) with flonicamid (B4), NANL (A7) with spinosad (B5), NANL (A7) with spiromesifen (B6), NANL (A7) with spirotetramat (B7), and NANL (A7) with thiamethoxam (B8).

In general, the weight ratio of component (A) to component (B) is from 2000:1 to 1:1000. In various embodiments, the weight ratio of component (A) to component (B) is from 100:1 to 1:100, from 50:1 to 1:50, from 20:1 to 1:50, from 20:1 to 1:20, from 10:1 to 1:50, from 1:1 to 1:50, from 1:1 to 1:40, from 1:1 to 1:35, from 1:1 to 1:30, from 1:1 to 1:25, from 1:1 to 1:20, from 1:1 to 1:15, from 1:1 to 1:10, from 1:1 to 1:5. For example, the weight ratio of component (A) to component (B) may be 1:100, 1:90, 1:80, 1:75, 1:70, 1:65, 1:60, 1:55, 1:50, 1:49, 1:48, 1:47, 1:46, 1:45, 1:44, 1:43, 1:42, 1:41, 1:40, 1:39, 1:38, 1:37, 1:36, 1:35, 1:34, 1:33, 1:32, 1:31, 1:30, 1:29, 1:28, 1:27, 1:26, 1:25, 1:24, 1:23, 1:22, 1:21, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 1:1.

The weight of component (A) refers to the total weight of loline analogs present in the composition.

In one embodiment, when component (B) is flonicamid, the weight ratio of (A) to (B) is from 1:3 to 1:100.

In one embodiment, when component (B) is thiamethoxam, the weight ratio of (A) to (B) is approximately 1:4.

In one embodiment, when component (B) is flonicamid, the weight ratio of (A) to (B) is from 1:15 to 1:6.25.

Certain weight ratios of component (A) to component (B) may give rise to synergistic activity. Therefore, according to a further aspect of the invention there is provided a composition, wherein component (A) and component (B) are present in the composition in amounts producing a synergistic effect. This synergistic activity is apparent from the fact that the activity of the composition comprising component (A) and component (B) is greater than the sum of the corresponding activities of component (A) and of component (B) alone. This synergistic activity extends the range of action of component (A) and component (B) in two ways. Firstly, the rates of application of component (A) and component (B) are lowered whilst the action remains equally good, meaning that the active ingredient mixture still achieves a high degree of pest control even where the two individual components have become totally ineffective in such a low application rate range. Secondly, there is a substantial broadening of the spectrum of pests that can be controlled.

A synergistic effect exists whenever the action of an active ingredient combination is greater than the sum of the actions of the individual components. The action to be expected E for a given active ingredient combination obeys the so-called COLBY formula and can be calculated as follows (COLBY, S. R. "Calculating synergistic and antagonistic responses of herbicide combination". Weeds, Vol. 15, pages 20-22 1967):
ppm=milligrams of active ingredient (a.i.) per liter
X=% action by first active ingredient using p ppm of the active ingredient
Y=% action by second active ingredient using q ppm of the active ingredient.
According to Colby, the expected (additive) action of active ingredients A+B using p+q ppm of active ingredient is $$E = X + Y - \frac{X \cdot Y}{100}$$

If the action actually observed O is greater than the expected action E, then the action of the combination is super-additive, i.e. there is a synergistic effect. In mathematical terms, synergism corresponds to a positive value for the difference of (O-E). In the case of purely complementary addition of activities (expected activity), said difference (O-E) is zero. A negative value of said difference (O-E) signals a loss of activity compared to the expected activity.

However, besides any synergistic action, the compositions according to the invention can also have further surprising advantageous properties. Examples of such advantageous properties that may be mentioned are: more advantageous degradability, improved toxicological and/or ecotoxicological behaviour, or improved characteristics of the useful plants including: emergence, crop yields, more developed root system, tillering increase, increase in plant height, bigger leaf blade, less dead basal leaves, stronger tillers, greener leaf colour, less fertilizers needed, less seeds needed, more productive tillers, earlier flowering, early grain maturity, less plant verse (lodging), increased shoot growth, improved plant vigour, and early germination.

Compositions of the present invention may be applied to a pest, plant, plant propagation material or plant growing locus either simultaneously (for example as a pre-formulated mixture or a tank mix), or sequentially in a suitable timescale. Co-application of components (A) and (B) has the added benefit of minimising farmer time spent applying products to crops. The combination may also encompass specific plant traits incorporated into the plant using any means, for example conventional breeding or genetic modification.

In one embodiment, the composition comprises an agriculturally acceptable formulation adjuvant. In a further embodiment, there is provided a composition consisting essentially of component (A), component (B) and an agri-culturally acceptable adjuvant. In a further embodiment, there is provided a composition consisting of component (A), component (B) and an agriculturally acceptable adjuvant. The compositions of the present invention are generally formulated using formulation adjuvants, such as carriers, solvents and surface-active agents (SFAs).

The compositions of the present invention may be useful for the control of pests, such as insects, diseases and weeds, in improving the tolerance of crop plants to abiotic stress conditions, and/or in improving the yield of crop plants. In one embodiment, the compositions of the present invention may be useful for the control of insect pests. The present invention provides a method for controlling pests in or on crop plants, improving the tolerance of crop plants to abiotic stress conditions, and/or improving the yield of crop plants, comprising treating the pests, plants, plant part, plant propagation material, or plant growing locus with a composition as described herein.

The present invention provides a method of controlling pests, comprising applying to the pest, or locus where the pest is present, a composition as described herein.

In one embodiment the pest is an insect or a mite or a nematode or a slug. In particular, the pest is an insect.

Examples of pest species which may be controlled by the present invention include: *Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (*thrips*), *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta migratoria* (locust), *Chortiocetes terminifera* (locust), *Diabrotica* spp. (rootworms), *Panonychus ulmi* (European red mite), *Panonychus citri* (citrus red mite), *Tetranychus urticae* (two spotted spider mite), *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides felis* (cat flea), *Liriomyza* spp. (leafminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the Mastotermitidae (for example *Mastotermes* spp.), the Kalotermitidae (for example Neotermes spp.), the Rhinotermitidae (for example *Coptotermes formosanus, Reticulitermes flavipes, R. speratu, R. virginicus, R. hesperus*, and *R. santonensis*) and the Termitidae (for example *Globitermes sulphureus*), *Solenopsis geminata* (fire ant), *Monomorium pharaonis* (pharaoh's ant), *Damalinia* spp. and *Linognathus* spp. (biting and sucking lice), *Meloidogyne* spp. (root knot nematodes), *Globodera* spp. and *Heterodera* spp. (cyst nematodes), *Pratylenchus* spp. (lesion nematodes), *Rhodopholus* spp. (banana burrowing nematodes), *Tylenchulus* spp. (citrus nematodes), *Haemonchus contortus* (barber pole worm), *Caenorhabditis elegans* (vinegar eelworm), *Trichostrongylus* spp. (gastro intestinal nematodes) and *Deroceras reticulatum* (slug).

In particular, compositions of the present invention may be used to control aphids (*Aphis gossypii, Myzus persicae, Dysaphis plantaginea, Aphis fabae, Aphis porni*), thrips (*Frankliniella occidentalis, Thrips tabaci, Scirtothrips dorsalis, Thrips parvispinus, Scirtothrips citri, Scirtothrips auranti*), whiteflies (*Bemisia tabaci, Bemisia argentifolli, Trialeurodes vaporarium*), leafminers (*Liriomyza trifolii, Tuta absoluta, Phyllocnistis citrella*), mites (*Tetranychus urticae, Panonychus citri, Aculops lycopersici*), stinkbugs (*Euchistus heros*), flies (*Musca domestica, Drosophila Suzuki, Ceratitis capitata*), psyllids (*Diaphorina citri, Psylla pyri*), weevils (*Ceutorhynchus suturalis*), beetles (*Leptinotarsa decemlineata, Phyllotreta* spp., *Pyrrhalta viburni*), bugs (*Creontiades pallidus*) and lepidoptera species. In one embodiment, compositions of the present invention are used to control sucking insect pests. In a further embodiment, compositions of the present invention are used to control *thrips* and/or whitefly. In a further embodiment, compositions of the present invention are used to control *Myzus persicae*.

In one embodiment, there is provided a method for controlling *Thrips tabaci* or *Myzus persicae* comprising contacting the pests with a composition comprising N-formylloline, N-acetylloline, and N-acetylnorloline (A1) and flonicamid (B4).

In one embodiment, there is provided a method for controlling *Myzus persicae* comprising contacting the pests with a composition comprising N-formylloline, N-acetylloline, and N-acetylnorloline (A1) and thiamethoxam (B8).

The present invention provides a method of improving the tolerance of a plant to abiotic stress, wherein the method comprises applying to the plant, plant part, plant propagation material, or plant growing locus a composition as described herein.

The present invention provides a method for regulating or improving the growth of a plant, wherein the method comprises applying to the plant, plant part, plant propagation material, or plant growing locus a composition as described herein. In one embodiment, plant growth is regulated or improved when the plant is subject to abiotic stress conditions.

The term "regulating or improving the growth of a crop" means an improvement in plant vigour, an improvement in plant quality, improved tolerance to stress factors, and/or improved input use efficiency.

The term "plants" refers to all physical parts of a plant, including seeds, seedlings, saplings, roots, tubers, stems, stalks, foliage, and fruits.

The term "locus" as used herein means fields in or on which plants are growing, or where seeds of cultivated plants are sown, or where seed will be placed into the soil. It includes soil, seeds, and seedlings, as well as established vegetation.

The term "plant propagation material" denotes all generative parts of a plant, for example seeds or vegetative parts of plants such as cuttings and tubers. It includes seeds in the strict sense, as well as roots, fruits, tubers, bulbs, rhizomes, and parts of plants.

Where a range of numbers is disclosed herein (for example, 1 to 10), this is intended to include all numbers and intervening values within that range (for example, 1, 1.1, 2, 3, 3.9, 4, 5, 6, 6.5, 7, 8, 9 and 10) and also any sub-range of numbers and intervening values within that range (for example, 2 to 8, 1.5 to 5.5 and 3.1 to 4.7). Additionally, it is intended that the both the upper and lower limits specified are included within the range.

Where ranges or values used herein are preceded by the term "about", this term is intended to provide support for both the exact number that it precedes, and also a number that is near to or approximately the number that it precedes. In determining whether a number is near to or approximately a specifically recited number, the near or approximating number may be a number, which would be rounded to or be substantially equivalent to the specifically recited number. For example, the term "about 5" includes 5.0, 4.5, 5.4, 4.92, 5.01, and so on.

The composition can be in the form of concentrates which are diluted prior to use, although ready-to-use compositions can also be made. The final dilution is usually made with water, but can be made instead of, or in addition to, water, with, for example, liquid fertilisers, micronutrients, biological organisms, oil or solvents.

The compositions according to the invention are generally formulated in various ways using formulation adjuvants, such as carriers, solvents and surface-active substances. The formulations can be in various physical forms, e.g. in the form of dusting powders, gels, wettable powders, water-dispersible granules, water-dispersible tablets, effervescent pellets, emulsifiable concentrates, micro-emulsifiable concentrates, oil-in-water emulsions, oil-flowables, aqueous dispersions, oily dispersions, suspo-emulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO and WHO Specifications for Pesticides, United Nations, First Edition, Second Revision (2010). Such formulations can either be used directly or diluted prior to use. The dilutions can be made, for example, with water, liquid fertilisers, micronutrients, biological organisms, oil or solvents.

The formulations can be prepared e.g. by mixing the active ingredient with the formulation adjuvants in order to obtain compositions in the form of finely divided solids, granules, solutions, dispersions or emulsions. The active ingredients can also be formulated with other adjuvants, such as finely divided solids, mineral oils, oils of vegetable or animal origin, modified oils of vegetable or animal origin, organic solvents, water, surface-active substances or combinations thereof.

The active ingredients can also be contained in very fine microcapsules. Microcapsules contain the active ingredients in a porous carrier. This enables the active ingredients to be released into the environment in controlled amounts (e.g. slow-release). Microcapsules usually have a diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes can comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art. Alternatively, very fine microcapsules can be formed in which the active ingredient is contained in the form of finely divided particles in a solid matrix of base substance, but the microcapsules are not themselves encapsulated.

The formulation adjuvants that are suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol, propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydro-furfuryl alcohol, hexanol, octanol, ethylene glycol, propylene glycol, glycerol, N-methyl-2-pyrrolidone and the like.

Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances.

A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate salts of alkylarylsulfonates, such as calcium dodecyHbenzenesulfonate alkylphenol/alkylene oxide addition products, such as nonylphenol ethoxylate alcohol/alkylene oxide addition products, such as tridecylalcohol ethoxylate soaps, such as sodium stearate salts of alkylnaphthalenesulfonates, such as sodium dibutylnaphthalenesulfonate dialkyl esters of sulfosuccinate salts, such as sodium di(2-ethylhexyl)sulfosuccinate sorbitol esters, such as sorbitol oleate quaternary amines, such as lauryltrimethylammonium chloride, polyethylene glycol esters of fatty acids, such as polyethylene glycol stearate block copolymers of ethylene oxide and propylene oxide and salts of mono and di-alkylphosphate esters and also further substances described e.g. in McCutcheon's Detergents and Emulsifiers Annual, MC Publishing Corp., Ridgewood N.J. (1981).

Further adjuvants that can be used in pesticidal formulations include crystallisation inhibitors, viscosity modifiers, suspending agents, dyes, anti-oxidants, foaming agents, light absorbers, mixing auxiliaries, antifoams, complexing agents, neutralising or pH-modifying substances and buffers, corrosion inhibitors, fragrances, wetting agents, take-up enhancers, micro-nutrients, plasticisers, glidants, lubricants, dispersants, thickeners, antifreezes, microbicides, and liquid and solid fertilisers.

The compositions according to the invention can include an additive comprising an oil of vegetable or animal origin, a mineral oil, alkyl esters of such oils or mixtures of such oils and oil derivatives. The amount of oil additive in the composition according to the invention is generally from 0.01 to 10%, based on the mixture to be applied. For example, the oil additive can be added to a spray tank in the desired concentration after a spray mixture has been prepared. Preferred oil additives comprise mineral oils or an oil of vegetable origin, for example rapeseed oil, olive oil or sunflower oil, emulsified vegetable oil, alkyl esters of oils of vegetable origin, for example the methyl derivatives, or an oil of animal origin, such as fish oil or beef tallow. Preferred oil additives comprise alkyl esters of C8 C22 fatty acids, especially the methyl derivatives of C12-C18 fatty acids, for example the methyl esters of lauric acid, palmitic acid and oleic acid (methyl laurate, methyl palmitate and methyl oleate, respectively). Many oil derivatives are known from the Compendium of Herbicide Adjuvants, 10th Edition, Southern Illinois University, 2010.

The inventive compositions generally comprise from 0.1 to 99% by weight, especially from 0.1 to 95% by weight, of compounds of the present invention and from 1 to 99.9% by weight of a formulation adjuvant which preferably includes from 0 to 25% by weight of a surface-active substance. Whereas commercial products may preferably be formulated as concentrates, the end user will normally employ dilute formulations. The rates of application vary within wide limits and depend on the nature of the soil, the method of application, the crop plant, the pest to be controlled, the prevailing climatic conditions, and other factors governed by the method of application, the time of application and the target crop. As a general guideline compounds may be applied at a rate of from 1 to 2000 l/ha, especially from 10 to 1000 l/ha.

Preferred formulations can have the following compositions (weight %):

Emulsifiable Concentrates:
active ingredient: 1 to 95%, preferably 60 to 90%
surface-active agent: 1 to 30%, preferably 5 to 20%
liquid carrier: 1 to 80%, preferably 1 to 35%
Dusts:
active ingredient: 0.1 to 10%, preferably 0.1 to 5%
solid carrier: 99.9 to 90%, preferably 99.9 to 99%
Suspension Concentrates:
active ingredient: 5 to 75%, preferably 10 to 50%
water: 94 to 24%, preferably 88 to 30%
surface-active agent: 1 to 40%, preferably 2 to 30%
Wettable Powders:
active ingredient: 0.5 to 90%, preferably 1 to 80%
surface-active agent: 0.5 to 20%, preferably 1 to 15%
solid carrier: 5 to 95%, preferably 15 to 90%

Granules:
active ingredient: 0.1 to 30%, preferably 0.1 to 15%
solid carrier: 99.5 to 70%, preferably 97 to 85%

The following Examples further illustrate, but do not limit, the invention.

| Wettable powders | a) | b) | c) |
|---|---|---|---|
| active ingredients | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The combination is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
|---|---|---|---|
| active ingredients | 25% | 50% | 75% |
| light mineral oil | 5% | 5% | 5% |
| highly dispersed silicic acid | 5% | 5% | — |
| Kaolin | 65% | 40% | — |
| Talcum | — | — | 20 |

The combination is thoroughly mixed with the adjuvants and the mixture is thoroughly ground in a suitable mill, affording powders that can be used directly for seed treatment.

| Emulsifiable concentrate | |
|---|---|
| active ingredients | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| Active ingredients | 5% | 6% | 4% |
| Talcum | 95% | — | — |
| Kaolin | — | 94% | — |
| mineral filler | — | — | 96% |

Ready-for-use dusts are obtained by mixing the combination with the carrier and grinding the mixture in a suitable mill. Such powders can also be used for dry dressings for seed.

| Extruder granules | |
|---|---|
| Active ingredients | 15% |
| sodium lignosulfonate | 2% |
| carboxymethylcellulose | 1% |
| Kaolin | 82% |

The combination is mixed and ground with the adjuvants, and the mixture is moistened with water. The mixture is extruded and then dried in a stream of air.

| Coated granules | |
|---|---|
| Active ingredients | 8% |
| polyethylene glycol (mol. wt. 200) | 3% |
| Kaolin | 89% |

The finely ground combination is uniformly applied, in a mixer, to the kaolin moistened with polyethylene glycol. Non-dusty coated granules are obtained in this manner.

| Suspension concentrate | |
|---|---|
| active ingredients | 40% |
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

| Flowable concentrate for seed treatment | |
|---|---|
| active ingredients | 40% |
| propylene glycol | 5% |
| copolymer butanol PO/EO | 2% |
| Tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of the combination are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed. The obtained capsule suspension is stabilized by adding 0.25 parts of a thickener and 3 parts of a dispersing agent. The capsule suspension formulation contains 28% of the active ingredients. The medium capsule diameter is 8-15 microns. The resulting formulation is applied to seeds as an aqueous suspension in an apparatus suitable for that purpose.

The composition of the present invention may be applied to a plant, part of the plant, plant organ, plant propagation material or a plant growing locus.

The application is generally made by spraying the composition, typically by tractor mounted sprayer for large areas, but other methods such as dusting (for powders), drip or drench can also be used. Alternatively the composition may be applied in furrow or directly to a seed before or at the time of planting.

The composition of the present invention may be applied pre-emergence or post-emergence. Where the composition is used to regulate the growth of crop plants or enhance the tolerance to abiotic stress, it may be applied post-emergence of the crop. Where the composition is used to inhibit or delay the germination of seeds, it may be applied pre-emergence. Where the composition is used to control pests, it may be applied as a preventative (before pest establishment) or curative (after pest establishment) treatment.

The present invention envisages application of the compositions of the invention to plant propagation material prior to, during, or after planting, or any combination of these. Although active ingredients can be applied to plant propagation material in any physiological state, a common approach is to use seeds in a sufficiently durable state to incur no damage during the treatment process. Typically, seed would have been harvested from the field removed from the plant and separated from any cob, stalk, outer husk, and surrounding pulp or other non-seed plant material. Seed would preferably also be biologically stable to the extent that treatment would not cause biological damage to the seed. It is believed that treatment can be applied to seed at any time between seed harvest and sowing of seed including during the sowing process.

Methods for applying or treating active ingredients on to plant propagation material or to the locus of planting are known in the art and include dressing, coating, pelleting and soaking as well as nursery tray application, in furrow application, soil drenching, soil injection, drip irrigation, application through sprinklers or central pivot, or incorporation into soil (broad cast or in band). Alternatively or in addition active ingredients may be applied on a suitable substrate sown together with the plant propagation material.

The rates of application of compositions of the present invention may vary within wide limits and depend on the nature of the soil, the method of application (pre- or post-emergence seed dressing application to the seed furrow no tillage application etc.), the crop plant, the prevailing climatic conditions, and other factors governed by the method of application, the time of application and the target crop. For foliar or drench application, the compositions of the present invention are generally applied at a rate of from 1 to 2000 g/ha, especially from 5 to 1000 g/ha. For seed treatment the rate of application is generally between 0.0005 and 150 g per 100 kg of seed.

The compositions of the present invention may be applied to dicotyledonous or monocotyledonous crops. Crops of useful plants in which the composition according to the invention can be used include perennial and annual crops, such as berry plants for example blackberries, blueberries, cranberries, raspberries and strawberries cereals for example barley, maize (corn), millet, oats, rice, rye, sorghum triticale and wheat fibre plants for example cotton, flax, hemp, jute and sisal field crops for example sugar and fodder beet, coffee, hops, mustard, oilseed rape (canola), poppy, sugar cane, sunflower, tea and tobacco fruit trees for example apple, apricot, avocado, banana, cherry, citrus, nectarine, peach, pear and plum grasses for example Bermuda grass, bluegrass, bentgrass, centipede grass, fescue, ryegrass, St. Augustine grass and Zoysia grass herbs such as basil, borage, chives, coriander, lavender, lovage, mint, oregano, parsley, rosemary, sage and thyme legumes for example beans, lentils, peas and soya beans nuts for example almond, cashew, ground nut, hazelnut, peanut, pecan, pistachio and walnut palms for example oil palm ornamentals for example flowers, shrubs and trees other trees, for example cacao, coconut, olive and rubber vegetables for example asparagus, aubergine, broccoli, cabbage, carrot, cucumber, garlic, lettuce, marrow, melon, okra, onion, pepper, potato, pumpkin, rhubarb, spinach and tomato and vines for example grapes.

Crops are to be understood as being those which are naturally occurring, obtained by conventional methods of breeding, or obtained by genetic engineering. They include crops which contain so-called output traits (e.g. improved storage stability, higher nutritional value and improved flavour).

Crops are to be understood as also including those crops which have been rendered tolerant to herbicides like bromoxynil or classes of herbicides such as ALS-, EPSPS-, GS-, HPPD- and PPO-inhibitors. An example of a crop that has been rendered tolerant to imidazolinones, e.g. imazamox, by conventional methods of breeding is Clearfield® summer canola. Examples of crops that have been rendered tolerant to herbicides by genetic engineering methods include e.g. glyphosate- and glufosinate-resistant maize varieties commercially available under the trade names RoundupReady®, Herculex I® and LibertyLink®.

Crops are also to be understood as being those which naturally are or have been rendered resistant to harmful insects. This includes plants transformed by the use of recombinant DNA techniques, for example, to be capable of synthesising one or more selectively acting toxins, such as are known, for example, from toxin-producing bacteria. Examples of toxins which can be expressed include d-endotoxins, vegetative insecticidal proteins (Vip), insecticidal proteins of bacteria colonising nematodes, and toxins produced by scorpions, arachnids, wasps and fungi.

An example of a crop that has been modified to express the *Bacillus thuringiensis* toxin is the Bt maize KnockOut (Syngenta Seeds). An example of a crop comprising more than one gene that codes for insecticidal resistance and thus expresses more than one toxin is VipCot® (Syngenta Seeds). Crops or seed material thereof can also be resistant to multiple types of pests (so-called stacked transgenic events when created by genetic modification). For example, a plant can have the ability to express an insecticidal protein while at the same time being herbicide tolerant, for example Herculex I® (Dow AgroSciences, Pioneer Hi-Bred International).

Normally, in the management of a crop a grower would use one or more other agronomic chemicals or biologicals in addition to the composition of the present invention.

The present invention also provides the use of the composition as defined above for controlling insect pests.

EXAMPLES

Tests were conducted to determine the efficacy of certain compositions of the present invention.

Test Solutions

Component (A1) is a mixture of NAL, NFL and NANL in a weight ratio of about approximately 1:4:2. Stock solutions of thiamethoxam and flonicamid were prepared respectively by dissolving the technical active ingredient in DMSO. The aqueous test solutions were prepared by mixing together the appropriate stock solutions to the desired concentrations.

Tests Against *Myzus persicae*

Sunflower leaf discs were placed on agar in a 24-well microtiter plate and sprayed with aqueous test solutions prepared from DMSO stock solutions. After drying, the leaf discs were infested with an aphid population of mixed ages. The samples were assessed for mortality 6 days after infestation.

Tests Against *Thrips tabaci*

Sunflower leaf discs were placed on agar in 24-well microtiter plates and sprayed with aqueous test solutions prepared from DMSO stock solutions. After drying, the leaf discs were infested with a *thrips* population of mixed ages. The samples were assessed for mortality 6 days after infestation.

The results are shown in the Tables below.

TABLE 1

Compositions where (B) is thiamethoxam, for control of *Myzus persicae*

| Active ingredients | | Concentration (ppm AI) | | % Mortality | | |
|---|---|---|---|---|---|---|
| Component (B) | Component (A) | Component (B) | Component (A) | Measured | Expected | Difference |
| Thiamethoxam | — | 1.6 | | 45 | | |
| Thiamethoxam | — | 0.8 | | 0 | | |
| Thiamethoxam | — | 0.4 | | 0 | | |
| — | A1 | | 312.5 | 60 | | |
| — | A1 | | 156.25 | 0 | | |
| Thiamethoxam | A1 | 1.6 | 312.5 | 90 | 78 | 12 |
| Thiamethoxam | A1 | 1.6 | 156.25 | 90 | 45 | 45 |
| Thiamethoxam | A1 | 0.8 | 312.5 | 90 | 60 | 30 |
| Thiamethoxam | A1 | 0.8 | 156.25 | 10 | 0 | 10 |
| Thiamethoxam | A1 | 0.4 | 312.5 | 25 | 60 | −35 |
| Thiamethoxam | A1 | 0.4 | 156.25 | 40 | 0 | 40 |

TABLE 2

Compositions where (B) is flonicamid, for control of *Thrips tabaci*

| Active ingredients | | Concentration (ppm AI) | | % Mortality | | |
|---|---|---|---|---|---|---|
| Component (B) | Component (A) | Component (B) | Component (A) | Measured | Expected | Difference |
| Flonicamid | — | 200 | | 0 | | |
| Flonicamid | — | 100 | | 0 | | |
| — | A1 | | 625 | 0 | | |
| — | A1 | | 312.5 | 0 | | |
| Flonicamid | A1 | 200 | 625 | 80 | 0 | 80 |
| Flonicamid | A1 | 200 | 312.5 | 0 | 0 | 0 |
| Flonicamid | A1 | 100 | 625 | 0 | 0 | 0 |
| Flonicamid | A1 | 100 | 312.5 | 20 | 0 | 20 |

TABLE 3

Compositions where (B) is flonicamid, for control of *Myzus persicae*

| Active ingredients | | Concentration (ppm AI) | | % Mortality | | |
|---|---|---|---|---|---|---|
| Component (B) | Component (A) | Component (B) | Component (A) | Measured | Expected | Difference |
| Flonicamid | — | 12.5 | | 90 | | |
| Flonicamid | — | 6.25 | | 65 | | |

TABLE 3-continued

Compositions where (B) is flonicamid, for control of *Myzus persicae*

| Active ingredients | | Concentration (ppm AI) | | % Mortality | | |
|---|---|---|---|---|---|---|
| Component (B) | Component (A) | Component (B) | Component (A) | Measured | Expected | Difference |
| Flonicamid | — | 3.125 | | 0 | | |
| — | A1 | | 312.5 | 60 | | |
| — | A1 | | 156.25 | 0 | | |
| Flonicamid | A1 | 12.5 | 312.5 | 95 | 96 | −1 |
| Flonicamid | A1 | 12.5 | 156.25 | 100 | 90 | 10 |
| Flonicamid | A1 | 12.5 | 78.125 * | 95 | 90 | 5 |
| Flonicamid | A1 | 6.25 | 312.5 | 95 | 86 | 9 |
| Flonicamid | A1 | 6.25 | 156.25 | 95 | 65 | 30 |
| Flonicamid | A1 | 6.25 | 78.125 * | 80 | 65 | 15 |
| Flonicamid | A1 | 6.25 | 39.0625 * | 75 | 65 | 10 |
| Flonicamid | A1 | 3.125 | 312.5 | 80 | 60 | 20 |
| Flonicamid | A1 | 3.125 | 156.25 | 40 | 0 | 40 |
| Flonicamid | A1 | 3.125 | 78.125 * | 70 | 0 | 70 |
| Flonicamid | A1 | 3.125 | 39.0625 * | 50 | 0 | 50 |
| Flonicamid | A1 | 3.125 | 19.53125 * | 25 | 0 | 25 |

* The rate of Component (A) was lower than the lowest rate tested in solo treatments. Since no activity was observed at a rate of 156 ppm, Component (A) would also not exhibit activity at lower concentrations. Mixture combinations having lower concentrations of component (A) that are not listed in the table were not tested.

The invention claimed is:

1. A composition comprising a synergistic ratio of (A) at least one loline alkaloid selected from the group comprising N-acetylloline, N-formylloline, N-acetylnorloline, and mixtures thereof, and (B) a pesticide selected from the group consisting of flonicamid and thiamethoxam.

2. A composition according to claim 1 further comprising one or more formulation adjuvants.

3. A composition according to claim 1, wherein component (A) comprises N-formylloline and N-acetylloline.

4. A composition according to claim 1, wherein component (A) comprises N-acetylloline, N-formylloline, and N-acetylnorloline in a weight ratio from 1:3:1 to 1:6:3.

5. A composition according to claim 1 wherein component (B) is flonicamid, and the weight ratio of (A) to (B) is from 1:3 to 1:100.

6. A method of controlling *Thrips tabaci* or *Myzus persicae* pests comprising contacting the pests with the composition of claim 5.

7. A composition according to claim 1 wherein component (B) is thiamethoxam and the weight ratio of (A) to (B) is 1:4.

8. A method of controlling *Myzus persicae* pests comprising contacting the pests with the composition of claim 7.

* * * * *